US012796983B2

(12) United States Patent
Burashnikov et al.

(10) Patent No.: US 12,796,983 B2
(45) Date of Patent: Nov. 17, 2026

(54) METHODS AND SYSTEMS FOR EYE GAZE METRIC DETERMINATION AND PSYCHOPHYSIOLOGICAL STATE DETECTION

(71) Applicant: Harman International Industries, Incorporated, Stamford, CT (US)

(72) Inventors: Evgenii Pavlovich Burashnikov, Yerevan (AM); Nikita Timakin, Yerevan (AM); Ivan Sergeevich Shishalov, Nizhniy Novgorod (RU); Anastasiya Vladimirovna Bakhchina, Nizhny Novgorod (RU); Andrey Viktorovich Filimonov, Novi, MI (US); Karina Arutyunova, Cirencester (GB); Anastasiya Sergeevna Filatova, Balakhna (RU)

(73) Assignee: HARMAN INTERNATIONAL INDUSTRIES, INCORPORATED, Stamford, CT (US)

( * ) Notice: Subject to any disclaimer, the term of this patent is extended or adjusted under 35 U.S.C. 154(b) by 238 days.

(21) Appl. No.: 18/627,335

(22) Filed: Apr. 4, 2024

(65) Prior Publication Data

US 2025/0311953 A1 Oct. 9, 2025

(51) Int. Cl.

*A61B 5/18* (2006.01)
*A61B 5/00* (2006.01)
(Continued)

(52) U.S. Cl.

CPC .............. *A61B 5/18* (2013.01); *A61B 5/0077* (2013.01); *A61B 5/1103* (2013.01); *A61B 5/163* (2017.08); *A61B 5/7264* (2013.01)

(58) Field of Classification Search

USPC .................................................. 382/103, 128
See application file for complete search history.

(56) References Cited

U.S. PATENT DOCUMENTS

| | | | |
|---|---|---|---|
| 6,090,051 | A | 7/2000 | Marshall |
| 6,102,870 | A | 8/2000 | Edwards |

(Continued)

FOREIGN PATENT DOCUMENTS

| | | | |
|---|---|---|---|
| WO | 2006024129 | A1 | 3/2006 |
| WO | 2008107832 | A1 | 9/2008 |
| WO | 2015116832 | A1 | 8/2015 |

OTHER PUBLICATIONS

Jyotsna et al. PredictEye: Personalized Time Series Model for Mental State Prediction Using Eye Tracking, IEEE Access, Digital Object Identifier 10.1109/ACCESS.2023.3332762, pp. 128383-128409 . (Year: 2023).*

(Continued)

*Primary Examiner* — Ishrat I Sherali
(74) *Attorney, Agent, or Firm* — McCoy Russell LLP

(57) ABSTRACT

Disclosed herein are methods and systems for real-time detection of psychophysiological states from eye movement data. The methods involve capturing eye gaze vectors and eyelid openness levels over time using a user-facing camera. A sequence of discrete eye behaviors, including saccades, fixations, blinks, and long closures, is determined from the eye gaze vectors and eyelid openness levels. The sequence of discrete eye behaviors is transformed into a machine readable representation using a sliding time window. A mathematical or machine learning model then maps the machine readable representation of eye behaviors to one or more psychophysiological states. This approach provides a computationally efficient mechanism for predicting psychophysiological states by compressing gaze data into a continuous, numerical representation of eye behavioral events correlated with human psychophysiological states, including drowsiness, cognitive load, stress, and others.

10 Claims, 7 Drawing Sheets

(51) Int. Cl.
*A61B 5/11* (2006.01)
*A61B 5/16* (2006.01)

(56) References Cited

U.S. PATENT DOCUMENTS

| | | | | |
|---|---|---|---|---|
| 7,344,251 | B2 | 3/2008 | Marshall | |
| 7,435,227 | B2 | 10/2008 | Farbos | |
| 7,438,418 | B2 | 10/2008 | Farbos | |
| 7,460,940 | B2 * | 12/2008 | Larsson | G06V 40/18 701/45 |
| 7,938,785 | B2 | 5/2011 | Aguilar et al. | |
| 8,487,775 | B2 * | 7/2013 | Victor | A61B 5/163 340/576 |
| 9,646,046 | B2 | 5/2017 | Sadowsky et al. | |
| 9,723,992 | B2 | 8/2017 | Senechal et al. | |
| 9,763,573 | B2 | 9/2017 | Distasi et al. | |
| 9,934,425 | B2 | 4/2018 | el Kaliouby et al. | |
| 10,111,611 | B2 | 10/2018 | el Kaliouby et al. | |
| 10,966,605 | B2 * | 4/2021 | Komogortsev | A61B 5/4076 |
| 11,269,420 | B1 * | 3/2022 | Marti | G06V 20/597 |
| 11,640,572 | B2 * | 5/2023 | Zakariaie | G06Q 10/0635 382/155 |
| 2007/0066916 | A1 | 3/2007 | Lemos | |
| 2008/0150734 | A1 | 6/2008 | Johns | |
| 2010/0033333 | A1 * | 2/2010 | Victor | A61B 5/7264 340/576 |
| 2018/0125356 | A1 | 5/2018 | Yamada | |
| 2018/0125405 | A1 | 5/2018 | Yamada | |
| 2018/0125406 | A1 | 5/2018 | Yamada | |
| 2019/0077409 | A1 * | 3/2019 | Zandi | G06F 3/013 |
| 2021/0186395 | A1 * | 6/2021 | Zakariaie | G06Q 10/0635 |
| 2022/0117529 | A1 * | 4/2022 | Filimonov | A61B 5/18 |
| 2025/0349398 | A1 * | 11/2025 | Filimonov | A61B 5/165 |

OTHER PUBLICATIONS

Scholorholtz, B. et al., "Assessment of age differences in mental workload while driving using verbal versus visual-spatial subsidiary tasks," Proceedings of the Human Factors and Ergonomics Society Annual Meeting, vol. 50, No. 22, Oct. 2006, 5 pages.

"Driver Workload Metrics Project—Task 2 Final Report," NHTSA Website, Available Online at https://www.nhtsa.gov/sites/nhtsa.gov/files/documents/driver_workload_metrics_final_report.pdf, Nov. 2006, 460 pages.

Di Stasi, L. et al., "Saccadic velocity as an arousal index in naturalistic tasks," Neuroscience and Biobehavioral Reviews, vol. 37, No. 5, Jun. 2013, Available Online Mar. 26, 2013, 7 pages.

Shiferaw, B. et al., "Stationary gaze entropy predicts lane departure events in sleep-deprived drivers," Scientific Reports, vol. 8, No. 2220, Feb. 2, 2018, 10 pages.

Shiferaw, B. et al., "A review of gaze entropy as a measure of visual scanning efficiency," Neuroscience and Biobehavioral Reviews, vol. 96, Jan. 2019, 14 pages.

Ahlstrom, C. et al., "Comparison of 14 eye tracking systems with one and three cameras," MB '10: Proceedings of the 7th International Conference on Methods and Techniques in Behavioral Research, Eindhoven, Netherlands, Aug. 24, 2010, 4 pages.

Dong, Y. et al., "Driver Inattention Monitoring System for Intelligent Vehicles: A Review," IEEE Transactions on Intelligent Transportation Systems, vol. 12, No. 2, Jun. 2011, 19 pages.

You, F. et al., "Monitoring drivers' sleepy status at night based on machine vision," Multimedia Tools and Applications, vol. 76, No. 13, Nov. 5, 2016, 18 pages.

European Patent Office, Extended European Search Report Issued in Application No. 25165295.4, Jun. 27, 2025, Germany, 12 pages.

Babu, M. et al., "Estimating Pilots' Cognitive Load From Ocular Parameters Through Simulation and In-Flight Studies," Journal of Eye Movement Research, vol. 12, No. 3, Sep. 2, 2019, 16 pages.

Dorofte, A., "Video: How to create a feel-good atmosphere inside your new BMW," BMW Blog Website, Available Online at https://www.bmwblog.com/2019/11/09/video-how-to-create-a-feel-good-atmosphere-inside-your-new-bmw/, Nov. 9, 2019, 7 pages.

Savage, M. et al., "Mental health and movement behaviour during the Covid-19 pandemic in UK university students: Prospective cohort study," Mental Health and Physical Activity, vol. 19, Oct. 2020, 6 pages.

Ayres, P. et al., "The Validity of Physiological Measures to Identify Differences in Intrinsic Cognitive Load," Frontiers in Psychology, vol. 12, Sep. 9, 2021, 16 pages.

"European New Car Assessment Programme (Euro NCAP)," Eruo NCAP Website, Available Online at https://www.euroncap.com/media/79883/euro-ncap-assessment-protocol-sa-safe-driving-v103.pdf, Dec. 2023, 37 pages.

* cited by examiner

METHODS AND SYSTEMS FOR EYE GAZE METRIC DETERMINATION AND PSYCHOPHYSIOLOGICAL STATE DETECTION

TECHNICAL FIELD

The present invention generally relates to the field of driver assistance systems and, more particularly, to methods and systems for extracting and processing eye gaze parameters to detect psychophysiological states of individuals, such as drivers, in real-time.

BACKGROUND

In recent years, the automotive industry has seen a significant increase in the development and implementation of Advanced Driver Assistance Systems (ADAS) aimed at enhancing vehicle safety and driver comfort. Among these systems, driver analytics have become a focal point, with a particular emphasis on monitoring and assessing the driver's psychophysiological state to detect and mitigate the risks associated with impaired driving due to factors such as fatigue, drowsiness, stress, and cognitive load.

Traditional methods for monitoring the psychophysiological state developed for medical and research use have relied on various physiological measures, including heart rate, skin conductance, and brain activity. However, these methods often require intrusive sensors that can be uncomfortable for the driver and may not always provide an accurate or timely assessment of the driver's state. At the same time, the psychophysiological state is not always apparent to an external observer or even to the individual experiencing it, which necessitates a continuous and objective monitoring system.

Eye gaze parameters have emerged as a promising means for assessing the psychophysiological state of drivers. Eye gaze data, encompassing direction of gaze, and position of various eye features (e.g., eyelids) have been shown to correlate with changes in human states, particularly related to cognitive load levels. Despite the potential of eye gaze data, the extraction and processing of such data to reliably determine the psychophysiological state of drivers presents considerable computational challenges. The computational complexity of accurately interpreting eye gaze data is compounded by the need to process this gaze data to predict psychophysiological states in substantially real-time.

The current disclosure addresses these challenges by providing systems and methods for extracting quantitative but compact representations of eye behaviors which are strongly correlated with human psychophysiological states. The current disclosure aims to overcome the limitations of current implementations and offer an approach that is applicable in real-world scenarios, such as driver monitoring systems.

SUMMARY

In one embodiment, a method for detecting psychophysiological states from eye movement data is provided. The method includes capturing, via a user-facing camera, a sequence of eye gaze vectors and eyelid openness levels over time. A plurality of second order eye movement metrics are determined from the eye gaze vectors and eyelid openness levels, wherein the plurality of second order eye movement metrics are indicative of discrete eye behaviors. The method further includes transforming the plurality of second order eye movement metrics into a machine readable representation within a pre-determined time window. Additionally, the method involves predicting, via mathematical approaches, including but not limited to use of trained machine learning models, one or more psychophysiological states using the machine readable representation of the plurality of second order eye movement metrics.

In another embodiment, a method is disclosed that includes receiving a time sequence of eye gaze vectors and eyelid openness levels of a user. The method includes transforming the time sequence of eye gaze vectors and eyelid openness levels to a sequence of discrete eye behaviors, including one or more of saccades, fixations, blinks, and long closures. Metainformation associated with each of the discrete eye behaviors is determined. The method also includes converting the sequence of discrete eye behaviors into a machine readable representation of eye behaviors using a sliding time window. Furthermore, the method comprises mapping the machine readable representation of eye behaviors via mathematical modelling, e.g., machine learning, to one or more psychophysiological states.

According to yet another embodiment of the present disclosure, a system for detecting psychophysiological states from eye movement data is provided. The system comprises a camera configured to capture a sequence of eye gaze vectors and eyelid openness levels over time. A non-transitory memory stores instructions and a machine learning model. A processor, communicably coupled to the camera and the non-transitory memory, is configured to determine a plurality of second order eye movement metrics from the eye gaze vectors and eyelid openness levels, wherein the plurality of second order eye movement metrics are indicative of discrete eye behaviors. The processor is further configured to transform the plurality of second order eye movement metrics into a machine readable representation of the plurality of second order eye movement metrics within a pre-determined time window. Additionally, the processor is configured to predict one or more psychophysiological states using methods of mathematical analysis, including machine learning, based on the machine readable representation of the plurality of second order eye movement metrics.

The embodiments disclosed herein provide for a robust system and method for detecting psychophysiological states, such as drowsiness, cognitive overload, and stress, by analyzing eye movement data. The disclosed techniques allow for the transformation of eye movement metrics into a compact, quantitative, and machine readable representation that can be effectively utilized by mathematical modeling techniques such as machine learning, to predict various psychophysiological states, thereby enhancing the understanding and interpretation of a user's mental and emotional state.

DETAILED DESCRIPTION

Examples will be provided below for illustration. The descriptions of the various examples will be presented for purposes of illustration, but are not intended to be exhaustive or limited to the embodiments. Many modifications and variations will be apparent to those of ordinary skill in the art without departing from the scope and spirit of the described embodiments.

The current disclosure provides systems and methods for the extraction and processing of eye movement data to detect psychophysiological states of individuals. The current disclosure encompasses methods and systems that capture eye gaze vectors and eyelid openness levels over time, transforming these into a set of second order eye movement metrics. These metrics serve as a computationally efficient encoding of eye movement data, offering interpretable and highly compact representations that are correlated with various psychophysiological states such as cognitive load, stress, and fatigue. In particular, the disclosed methods and systems facilitate the transformation of raw eye movement data into a machine readable representation within a predetermined time window. This machine readable representation is achieved through the determination of second order eye movement metrics, which include, but are not limited to, the number of blinks, number of fixations, overall fixation time, and average fixation time. These metrics are derived from discrete eye behaviors, such as saccades, fixations, and blinks, and are indicative of the user's psychophysiological state.

The technical advantage of the current disclosure lies in its ability to provide a compact, quantitative representation of eye movements that can be effectively utilized by machine learning models to predict various psychophysiological states. This approach significantly reduces the computational complexity typically associated with the real-time processing of eye gaze data. By converting the discrete sequence of eye movements into a continuous metric, the invention enables the efficient and accurate prediction of psychophysiological states, thereby enhancing the understanding and interpretation of a user's mental and emotional state.

Furthermore, the current disclosure addresses the challenge of accurately interpreting eye gaze data in substantially real-time, which is a significant computational challenge in the field of driver assistance systems and similar applications. The approaches disclosed herein may be applicable in driver monitoring systems, where the real-time assessment of a driver's state in a computationally constrained environment may be particularly advantageous. The compact and interpretable nature of the second order eye movement metrics makes them highly suitable for integration into existing systems, offering a significant improvement over traditional methods that may rely on more computationally complex metrics and/or more intrusive and less accurate measures of psychophysiological states.

Figure 1:
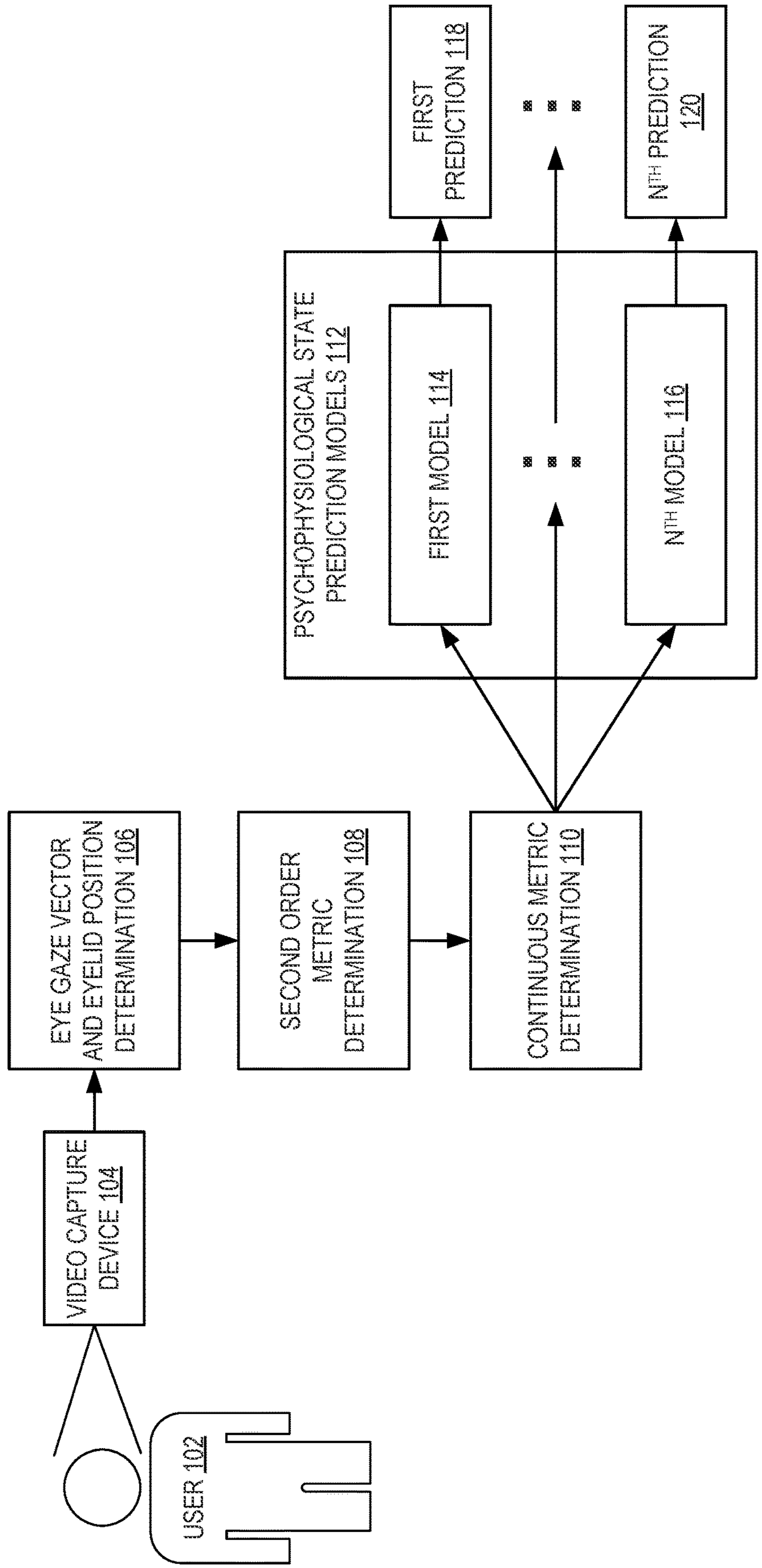
FIG. 1 is a schematic diagram illustrating an embodiment of a process for predicting psychophysiological states based on second order eye movement metrics of a user.
Figure 2:
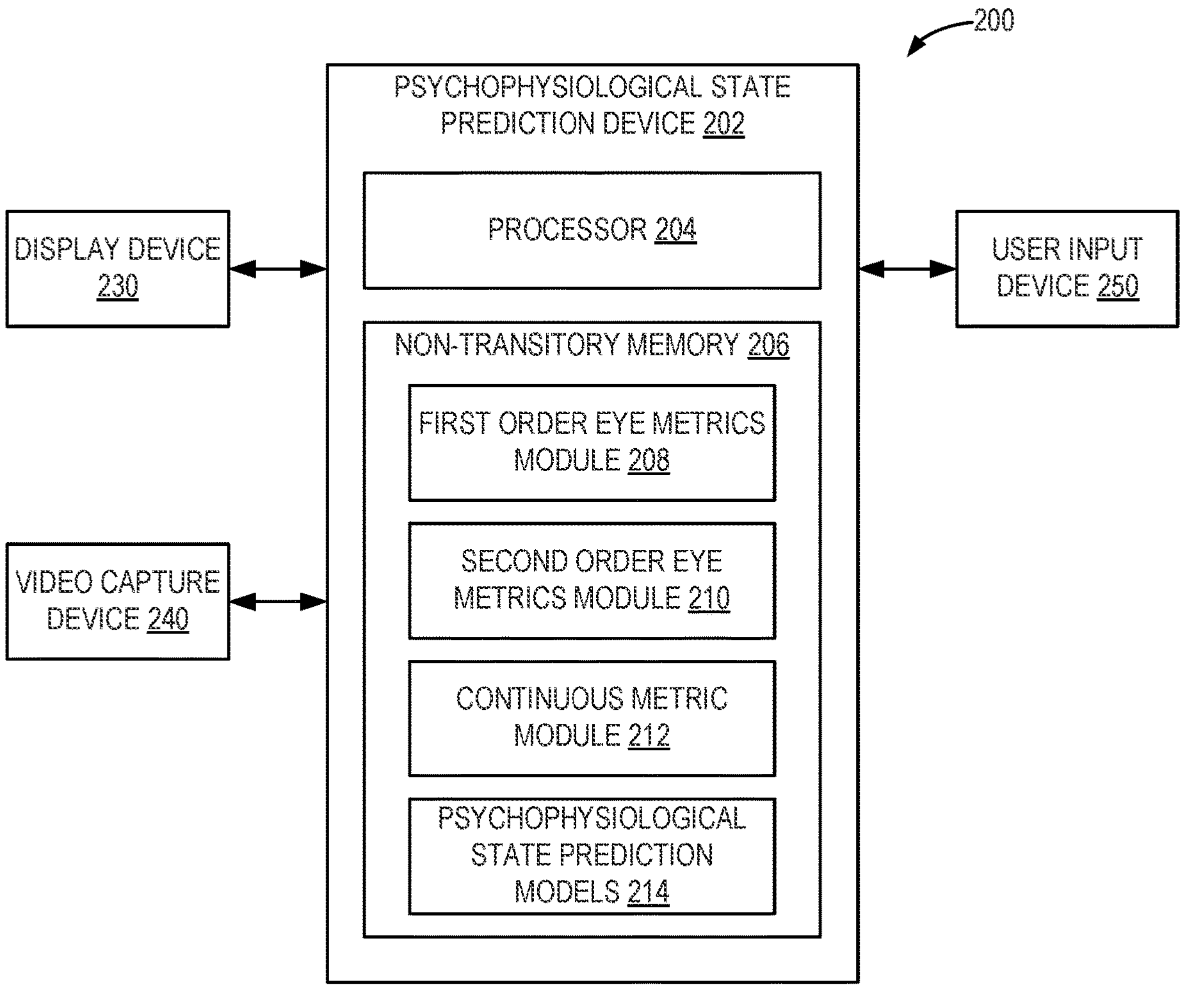
FIG. 2 is a block diagram depicting an embodiment of a psychophysiological state prediction device.
Figure 4:
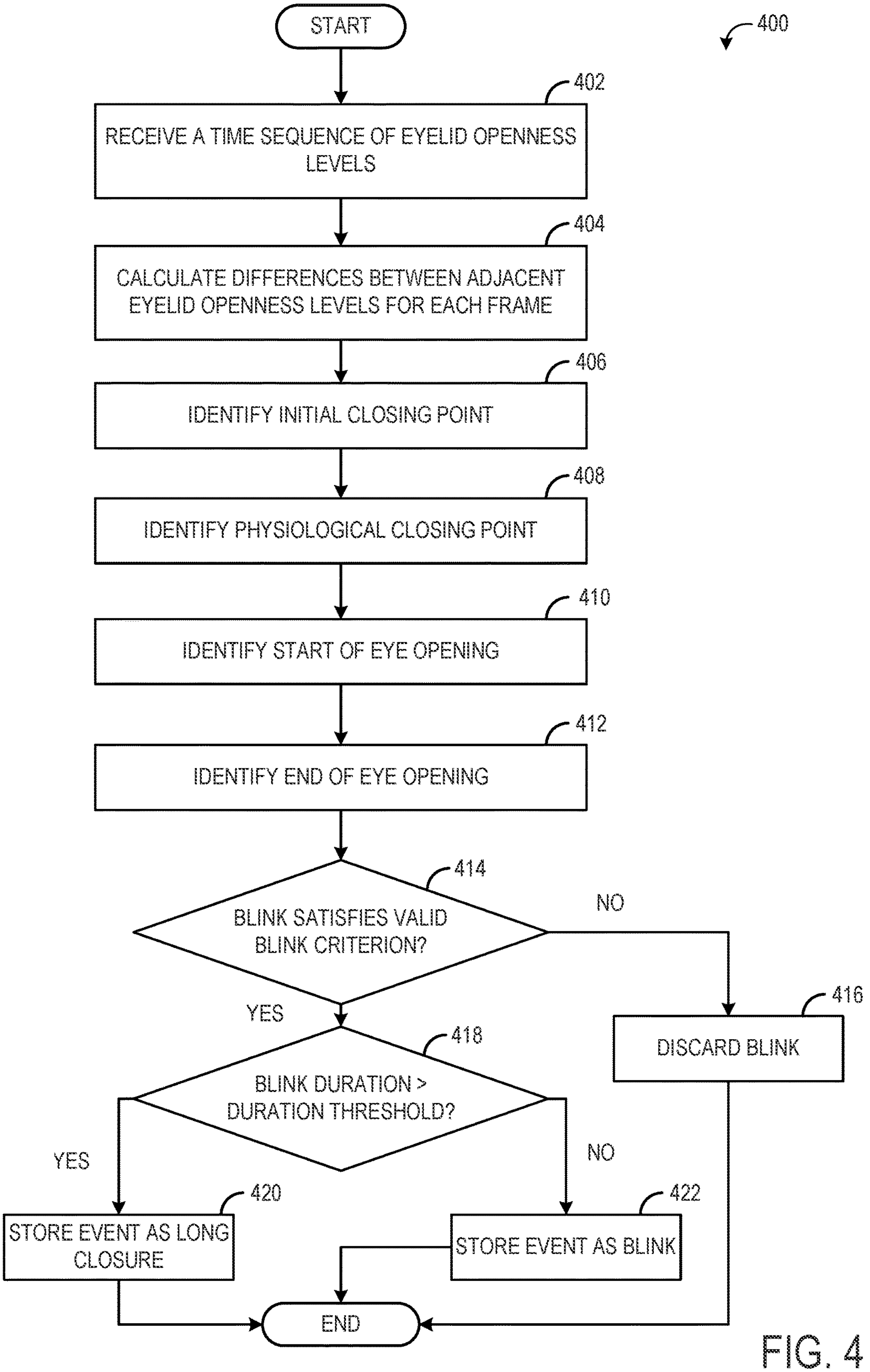
FIG. 4 is a flowchart of an embodiment of a method for identifying valid blinks and long closures from a time sequence of eyelid openness levels.
Figure 5:
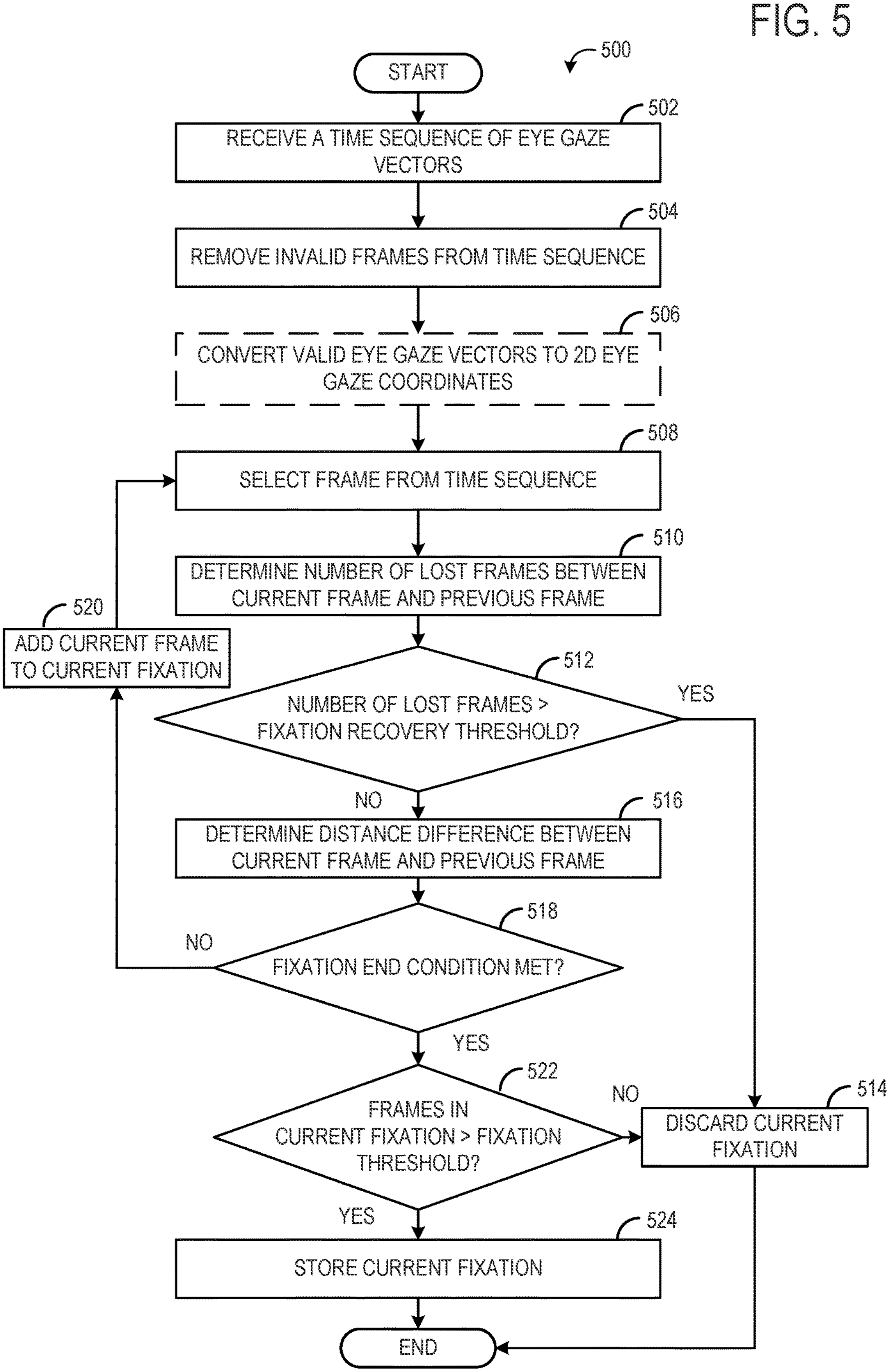
FIG. 5 is a flowchart of an embodiment of a method for determining fixations from a time sequence of eye gaze vectors.
Figure 6:
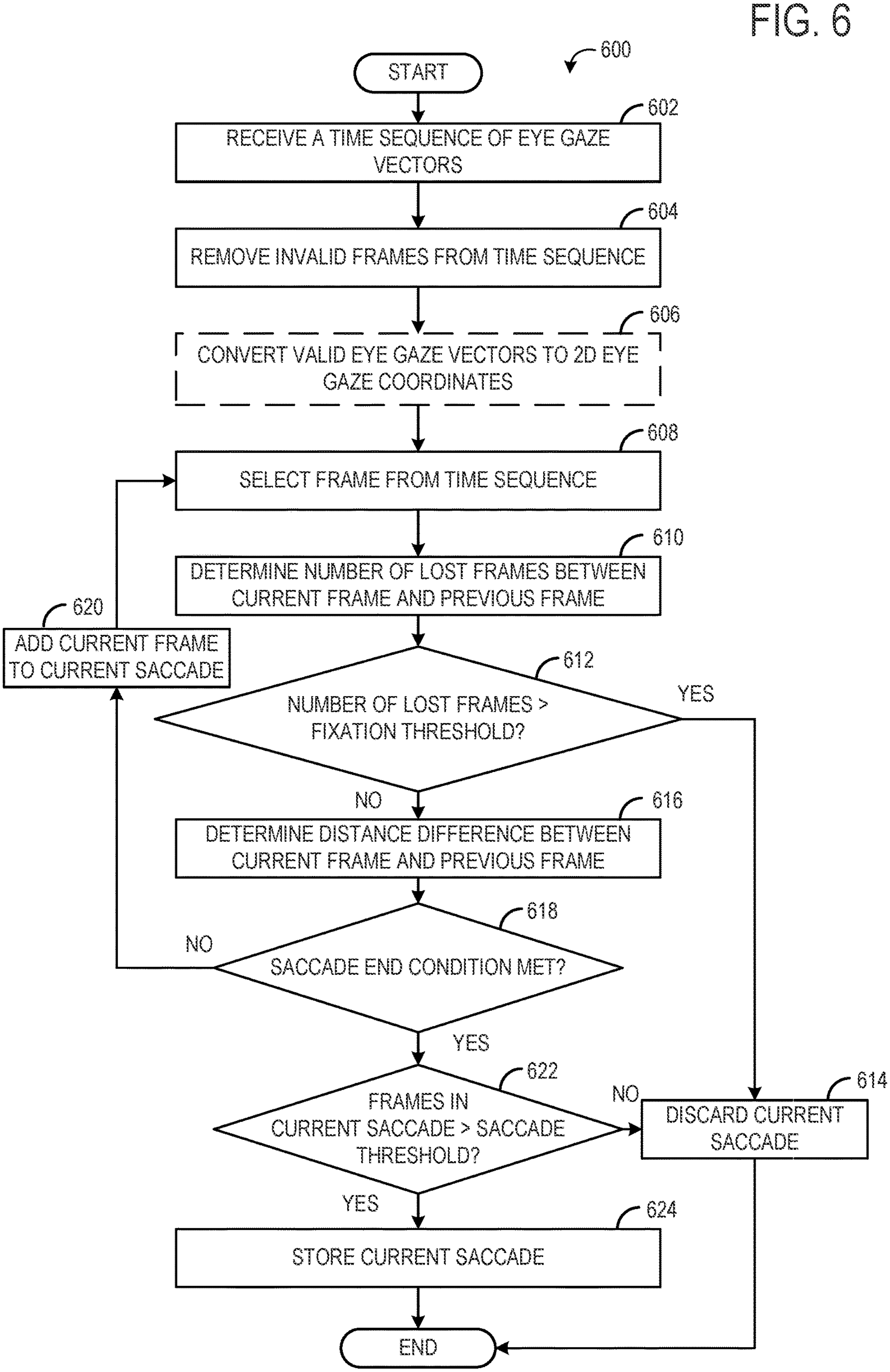
FIG. 6 is a flowchart of an embodiment of a method for determining saccades from a time sequence of eye gaze vectors.
Figure 7:
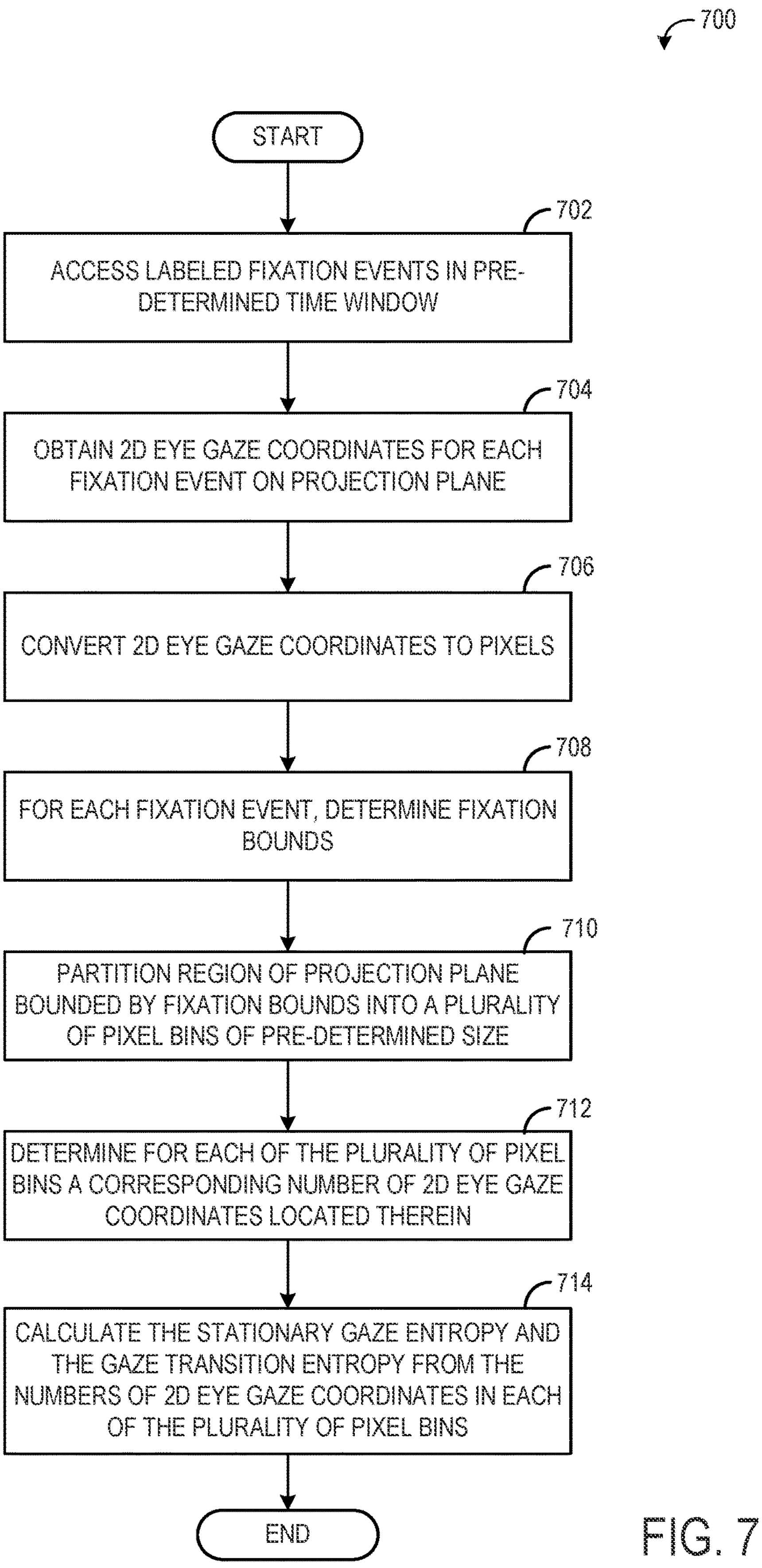
FIG. 7 is a flowchart of an embodiment of a method for calculating stationary gaze entropy and gaze transition entropy from 2D eye gaze coordinates within a predetermined time window.

One embodiment of a process for predicting psychophysiological states based on second order eye movement metrics of a user is depicted in FIG. 1. This process may be implemented by a psychophysiological state prediction device, as shown in FIG. 2, which is configured to analyze eye movement characteristics and derive second order eye movement metrics therefrom. The second order eye movement metrics are indicative of various psychophysiological states such as cognitive load or stress. The device and methods involved in this process are capable of transforming discrete sequences of eye movements into a machine readable representation that can be utilized for the prediction of psychophysiological states. The method for predicting one or more psychophysiological states for a user, based on machine readable representation of a plurality of second order eye movement metrics, is outlined in the flowchart of FIG. 3. This method includes the steps of capturing eye movement data, processing the data to extract second order eye movement metrics (as described in more detail in the descriptions of FIGS. 4-7), and applying machine learning algorithms to predict the user's psychophysiological state. FIG. 4 presents a flowchart of an embodiment of a method for identifying valid blinks and long closures from a time sequence of eyelid openness levels. This method enables distinguishing between different types of eye closures that may signal various states, such as drowsiness or momentary rest. The process of determining fixations from a time sequence of eye gaze vectors is illustrated in the flowchart of FIG. 5. Fixations are periods where the eye gaze remains relatively stable and are indicators of attention and cognitive processing. FIG. 6 depicts a flowchart of an embodiment of a method for determining saccades from a time sequence of eye gaze vectors. Saccades are rapid eye movements that occur as the eye jumps from one point of interest to another, and their patterns may be indicative of underlying psychophysiological states. Lastly, FIG. 7 provides a flowchart of an embodiment of a method for calculating stationary gaze entropy and gaze transition entropy from 2D eye gaze coordinates within a predetermined time window. These entropy measures offer a quantitative assessment of the user's visual scanning behavior and can be used to infer states such as fatigue or cognitive overload.

Referring to FIG. 1, a block diagram of a psychophysiological state detection process 100 is depicted, illustrating an embodiment of a system for predicting psychophysiological states based on eye movement metrics of a user.

The video capture device 104 is configured to capture video footage of the face of user 102. In one embodiment, the video capture device 104 may be a near-infrared (NIR) camera with a framerate of 60 fps, a view angle of 50-60 degrees, and a resolution of 1280×752. The camera is positioned to have a clear view of user 102's face, particularly the eye region, to facilitate accurate data capture. In another embodiment, the video capture device 104 may include advanced sensors capable of micromovement registration, enhancing the precision of the captured data. The video footage captured by the video capture device 104 serves as the raw data from which eye movement characteristics are extracted.

Eye gaze vector and eyelid position determination 106 segments eyelid positions in each frame of the video footage and determines eye gaze vectors for each frame. In one embodiment, this determination may involve the use of a eyetracker module or similar toolkit that derives eye gaze information from raw NIR video frames. The module may perform operations such as facebox detection, eyebox detection, head position detection, eyelid position detection, pupil detection (size and position), and the determination of the eye gaze vector itself. In another embodiment, the eye gaze vector and eyelid position determination 106 may employ machine learning algorithms to enhance the accuracy of the segmentation and vector determination, particularly in challenging lighting conditions or when user 102 exhibits a wide range of head movements.

Second order metric determination 108 determines a plurality of second order eye movement metrics from the eye gaze vectors and eyelid positions obtained from eye gaze vector and eyelid position determination 106. These metrics are indicative of discrete eye behaviors such as saccades, fixations, blinks, and long closures. In one embodiment, the second order metric determination 108 may calculate metainformation associated with each discrete eye behavior, including the length of the behavior, average gaze movement speed, and gaze fluctuation boundaries. In another embodiment, the second order metric determination 108 may identify blinks based on eyelid openness levels, where a blink comprises a contiguous portion of frames from the sequence of eyelid openness levels satisfying a blink criterion based on calculated differences between adjacent eyelid openness levels for each frame.

Machine readable metric determination 110 converts the sequence of discrete eye behaviors into a machine readable representation of eye behaviors using a sliding time window. This transformation prepares the data for analysis by the psychophysiological state prediction models 112. In one embodiment, machine readable metric determination 110 may include calculating a number of blinks, a number of fixations, and an overall fixation time within the pre-determined time window. In another embodiment, machine readable metric determination 110 may involve the use of continuous metrics such as the number of saccades, the overall saccade time, and the average saccade time, providing a nuanced representation of user 102's eye movement patterns over time.

Psychophysiological state prediction models 112 comprises a suite of machine learning models, including first model 114 through to an Nth model 116, each configured to predict one or more psychophysiological states using the machine readable representation of the plurality of second order eye movement metrics. In one embodiment, first model 114 may be a neural network-based classifier detecting the probability of high cognitive load or acute stress from the machine readable representation of the second order eye movement metrics. Additionally, these models are capable of generating output as per a more generalized state definition, where states of sleepiness, drowsiness, relaxed state, strained state, and stress can be represented as specific levels of arousal. This allows for a nuanced understanding of the user's psychophysiological condition beyond binary classifications. In another embodiment, Nth model 116 may be a deep learning model trained to predict drowsiness of the user 102, which could also be interpreted as a particular level of arousal. In some embodiments, psychophysiological state prediction models 112 may consist of only a single model; therefore, N may equal 1. In such embodiments, the single model may be configured to predict one, or a plurality of psychophysiological states, including an estimated arousal level that encompasses various states of user 102.

The output of the psychophysiological state prediction models 112 includes first prediction 118 and Nth prediction 120, which represent the predicted psychophysiological states of user 102. In one embodiment, first prediction 118 may indicate a binary state, such as the presence or absence of cognitive load, while Nth prediction 120 may provide a probabilistic assessment of user 102's drowsiness levels. Furthermore, in some embodiments the output of the psychophysiological state prediction models 112 model may comprise an estimated arousal level, which may be used directly as a measure of human state or further processed, for example, by applying specific thresholds, to determine if a subject is in a particular state such as sleepiness or stress. The estimated arousal level may be utilized either as a direct measure or to infer specific states through additional logic. In another embodiment, the predictions may be used to trigger alerts or interventions in real-time, such as in a driver monitoring system (DMS) or operator monitoring system (OMS), where the arousal level itself can be a critical parameter for ensuring safety and performance.

The psychophysiological state detection process 100, as described herein, enables substantially real-time detection of psychophysiological states by analyzing eye movement data. The disclosed techniques allow for the transformation of eye movement metrics into a compact, quantitative, and machine readable representation that can be effectively utilized by machine learning models to predict various psychophysiological states, thereby enhancing the understanding and interpretation of user 102's mental and emotional state.

Referring to FIG. 2, a psychophysiological state prediction system 200 for predicting a user's psychophysiological state based on eye metrics is shown. The system 200 is configured to analyze eye movement data and predict various psychophysiological states such as cognitive load or stress. This system is particularly advantageous in applications such as driver monitoring systems, where real-time assessment of the driver's state is desirable.

The psychophysiological state prediction system 200 includes a psychophysiological state prediction device 202. The prediction device 202 orchestrates the acquisition, processing, and analysis of eye movement data to predict the user's psychophysiological state. In one embodiment, the prediction device 202 may be integrated into a vehicle's advanced driver assistance system to monitor the driver's state continuously. In another embodiment, the prediction device 202 may be part of a standalone unit used in research settings to study the correlation between eye movements and psychophysiological states.

The processor 204 within the psychophysiological state prediction device 202 may be a multi-core processor capable of parallel processing to ensure real-time data analysis. In one embodiment, the processor 204 may be a specialized processor optimized for machine learning tasks, enabling the efficient execution of psychophysiological state prediction models. In another embodiment, the processor 204 may be a general-purpose processor that is part of a larger distributed computing system, such as a cloud-based service, where eye movement data is processed remotely.

Non-transitory memory 206 is a component of the psychophysiological state prediction device 202 that stores machine-readable instructions for the operation of the psychophysiological state prediction system 200. The non-transitory memory 206 houses several modules that employed in the prediction of psychophysiological states. In one embodiment, the non-transitory memory 206 may store a first order eye metrics module 208, which is responsible for determining eye gaze vectors and eyelid openness levels for each frame of video footage acquired by the video capture device 240. In another embodiment, the non-transitory memory 206 may include a second order eye metrics module 210 that derives second order eye movement metrics from the first order metrics, indicative of discrete eye behaviors such as saccades, fixations, and blinks.

The machine readable metric module 212, also stored within the non-transitory memory 206, is configured to transform the second order eye movement metrics into a machine readable representation within a predetermined time window. This module enables the system to calculate numerical metrics such as the number of blinks, number of fixations, and overall fixation time, which are essential for training machine learning algorithms. In one embodiment, the machine readable metric module 212 may utilize sliding time windows to generate metrics associated with every time unit, providing a nuanced view of the user's eye behavior over time.

Psychophysiological state prediction models 214 are a set of mathematical or machine learning models stored within the non-transitory memory 206. These models are trained to map the machine readable representation of eye behaviors to one or more psychophysiological states. In one embodiment, the models may include deep neural networks that learn correlations between the metrics and the ground truth of the subject's state. In another embodiment, the models may be based on support vector machines or other statistical learning methods that are capable of inferring states such as cognitive load or acute stress from the second order eye movement metrics.

The display device 230 is an output component of the psychophysiological state prediction system 200 that presents the results of the psychophysiological state predictions to the user. In one embodiment, the display device 230 may be a dashboard-mounted screen in a vehicle that alerts the driver to changes in their psychophysiological state. In another embodiment, the display device 230 may be part of a research setup, displaying real-time analytics of the participant's eye movements and inferred psychophysiological states.

The video capture device 240 captures video footage of the user from which the sequence of eye gaze vectors and eyelid openness levels are determined. In one embodiment, the video capture device 240 may be a near-infrared (NIR) camera with a high framerate, to ensure accurate and detailed capture of eye movements. In another embodiment, the video capture device 240 may include sensors configured for micromovement registration, providing a rich dataset for the prediction of psychophysiological states.

The user input device 250 allows for user interaction with the psychophysiological state prediction system 200. In one embodiment, the user input device 250 may be a touchscreen interface through which system settings can be adjusted or annotations can be made. In another embodiment, the user input device 250 may include a keyboard and mouse, enabling researchers to input additional data or control the system during experimental procedures.

Figure 3:
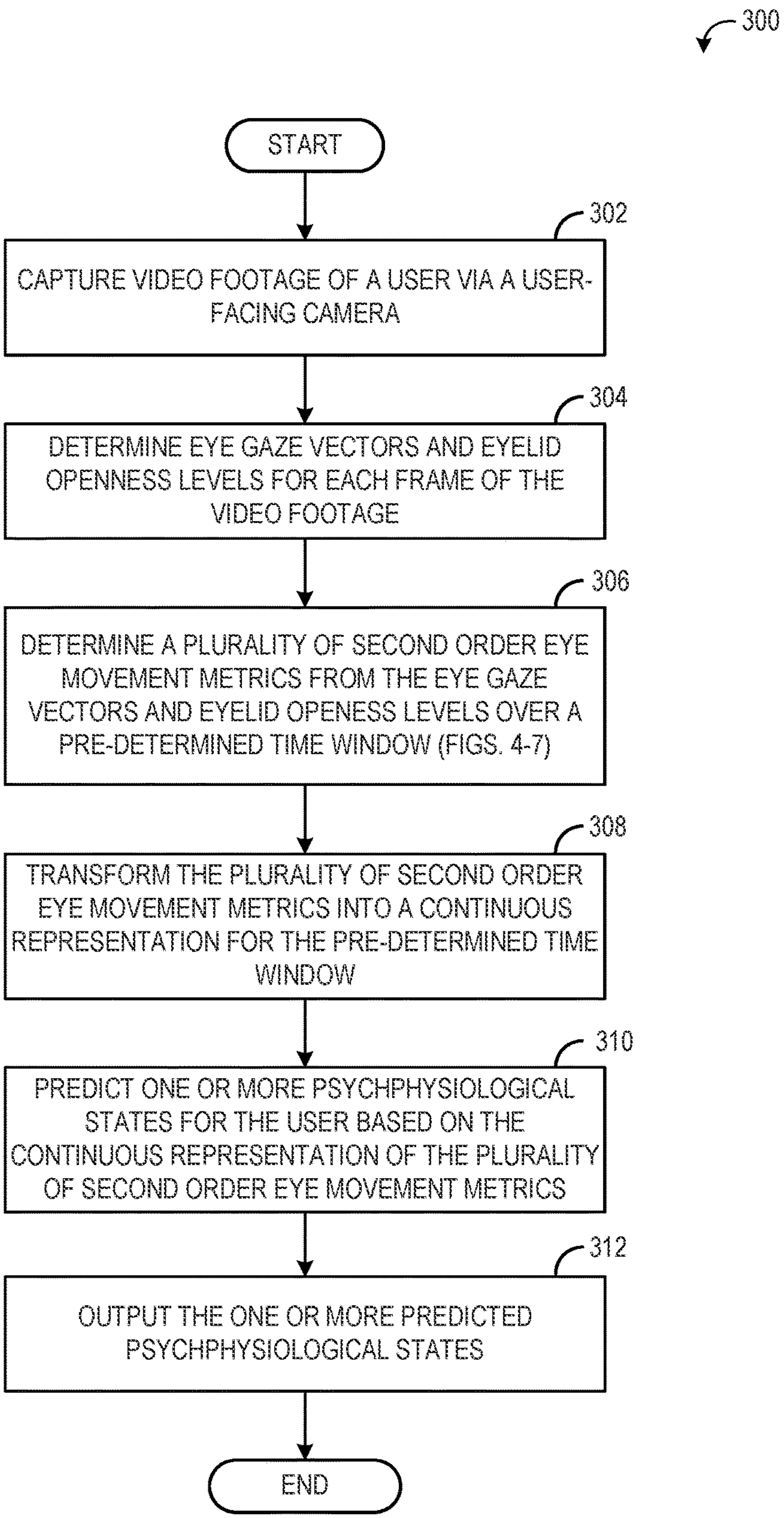
FIG. 3 is a flowchart of an embodiment of a method for predicting one or more psychophysiological states for a user based on machine readable representation of a plurality of second order eye movement metrics.

Referring to FIG. 3, a flowchart of a method 300 for predicting psychophysiological states of a user based on eye movement metrics is shown. The method 300 may be employed by a psychophysiological state prediction system to assess the mental and emotional state of a user, such as a driver, by analyzing eye movement data indicative of various psychophysiological states.

At operation 302, the system captures video footage of a user via a user-facing camera. The camera, which may be a Near-Infrared (NIR) camera with a framerate of 60 FPS, captures a sequence of images over time, providing raw data for subsequent analysis. In one embodiment, the camera may be integrated into a Driver Monitoring System (DMS) or an Operator Monitoring System (OMS) to monitor the user's eye movements in real-time. In another embodiment, the camera may be part of a laboratory setup for controlled observation studies related to cognitive load or stress detection.

Proceeding to operation 304, the system determines eye gaze vectors and eyelid openness levels for each frame of the video footage. This involves processing the captured images to extract the direction of the "virtual" vector coming from the center of the pupil and being normal to the surface of the eye, as well as the maximum distance between the upper and lower eyelids. In one embodiment, the eye gaze vectors may be represented as Euler angles or coordinates in three-dimensional space. In another embodiment, the eyelid openness levels may be measured in metric or angular coordinate systems, or presented as a degree of openness relative to the maximum possible level for each individual.

At operation 306, the system determines a plurality of second order eye movement metrics from the eye gaze vectors and eyelid openness levels over a pre-determined time window, as detailed in FIGS. 4-7. These metrics define eye behavioral patterns in time and include fixations, saccades, blinks, and long closures. Fixations are periods where the eye gaze remains relatively stable, indicating focused attention, and can be defined as the eye gaze being maintained within a small angular area, such as a 2-degree angle segment, for a duration exceeding a threshold, such as 100 milliseconds. Saccades are rapid eye movements that occur as the eye jumps from one point of interest to another, and their patterns may be indicative of underlying psychophysiological states. In one embodiment, saccades are identified by detecting eye movements that exceed a certain angular velocity threshold. In another embodiment, the system may also detect microsaccades, which are smaller, involuntary saccades that occur during fixations. Long closures, which may indicate drowsiness, are identified as periods where the eyelids remain closed for an extended duration, such as more than one second. In some embodiments, at operation 306 the system calculates metainformation for each behavioral pattern, including the length of the event, average gaze movement speed, and gaze fluctuation boundaries.

Operation 308 involves transforming the plurality of second order eye movement metrics into a machine readable representation for the pre-determined time window. This transformation includes converting the discrete sequence of saccades, fixations, and blinks into a numerical metric that defines the "amount" of patterns that occurred during the time window. In one embodiment, the machine readable representation may include characteristics such as the number of blinks, number of fixations, overall fixation time, and average fixation time. In another embodiment, the window may be sliding, allowing for the evaluation of numerical metrics within overlapping time windows, thereby providing metrics associated with every time unit.

At operation 310, the system predicts one or more psychophysiological states for the user based on the machine readable representation of the plurality of second order eye movement metrics. This prediction is facilitated by a machine learning model, which may include deep neural networks that learn correlations between the metrics and the ground truth of the user's psychophysiological state. In one embodiment, the model may be configured to infer whether a user is experiencing cognitive load or acute stress. In another embodiment, the model may be trained using machine readable representations derived from eye movement data to accurately predict states such as drowsiness or distraction.

At operation 312, the system outputs the one or more predicted psychophysiological states. This may include displaying the predicted states on a user interface or transmitting the information to a vehicle's central processing unit for real-time intervention. In one embodiment, the output may be used to alert the user or activate safety measures in response to detected states such as fatigue or high cognitive load. In another embodiment, the predicted states may be logged for further analysis or used to adjust the user's workload or environment to mitigate any detected impairments. Following operation 312, method 300 may end.

The method 300 provides a technical solution for real-time detection of psychophysiological states from eye movement data. The disclosed embodiments leverage advanced image processing techniques, second order metric derivation, and machine learning algorithms to predict various psychophysiological states, thereby enhancing the understanding and interpretation of a user's mental and emotional state.

Referring to FIG. 4, a method 400 for analyzing eyelid movements to identify blinks and long closures is shown. The method 400 enables processing time sequences of eyelid openness levels to accurately detect and categorize blinks and long closures, which are indicative of various psychophysiological states such as drowsiness or cognitive load. Method 400 may be executed by one or more systems disclosed herein, such as psychophysiological state prediction system 200.

At operation 402, the system receives a time sequence of eyelid openness levels. This sequence is captured via a user-facing camera, such as a near-infrared (NIR) camera, which records the maximum distance between the upper and lower eyelids over time. In one embodiment, the eyelid openness levels are extracted from video frames at a framerate corresponding to the camera's capabilities. The received data may be stored in a format such as CSV files, which include timestamped measurements of eyelid openness. In an alternative embodiment, the time sequence of eyelid openness levels may be received from a pre-processed dataset where the eyelid openness levels have been restored to a consistent framerate, ensuring temporal accuracy for subsequent analysis.

At operation 404, the system calculates differences between adjacent eyelid openness levels for each frame. This operation enables identifying the dynamic changes in eyelid position that characterize blinks and long closures. In one embodiment, the system computes the rate of change in eyelid openness by subtracting the openness level of a preceding frame from the current frame's level. A positive difference indicates eyelid opening, while a negative difference suggests eyelid closing. An alternative embodiment may apply smoothing algorithms to the time sequence data to mitigate the impact of noise and artifacts, thereby enhancing the precision of the calculated differences.

At operation 406, the system identifies an initial closing point, which marks the onset of a potential blink or long closure. This is achieved by detecting a frame where the calculated difference in eyelid openness levels falls below a pre-determined low-level closing threshold. In one embodiment, the low-level closing threshold may be set to a value such as −0.0005, which signifies an initial decrease in eyelid openness. Another embodiment may involve using machine learning classifiers to determine the initial closing point based on patterns observed in the eyelid movement data.

At operation 408 the system identifies the physiological closing point, which is a point in a blink or long closure where the eyelid is in a substantially closed position (i.e., the eyelids at a lowest point of descent in the blink or long closure and may be in contact). In one embodiment, the physiological closing point is found by searching for a frame following the initial closing point where the difference in eyelid openness levels is less than a high-level closing threshold, such as −0.001.

At operation 410, the system identifies the start of eye opening, by detecting a frame following the physiological closing point where the difference in eyelid openness levels exceeds a high-level opening threshold, indicative of the eye beginning to open. In one embodiment, the high-level opening threshold may be set to a value such as 0.0001. Another embodiment may use velocity thresholds derived from the eye movement data to determine the start of eye opening.

At operation 412, the system identifies the end of eye opening, which marks the completion of a blink or long closure event. This is determined by locating a frame after the start of eye opening where the difference in eyelid openness levels drops below a low-level opening threshold, such as 0.00012. In one embodiment, the system may calculate the duration of the eye opening phase to assist in identifying the end of eye opening. An alternative embodiment may employ pattern recognition algorithms to detect the stabilization of eyelid position, signaling the end of the event.

At operation 414, the system determines if the blink satisfies the valid blink criterion. If the event does not meet the criteria for a valid blink, the process proceeds to operation 416; otherwise, it continues to operation 418. In one embodiment, the valid blink criterion includes checking if the duration of the event falls within a range defined by minimum and maximum blink duration thresholds, such as 5 and 180 frames, respectively. An alternative embodiment may consider additional metainformation such as blink amplitude and velocity to validate the blink.

Operation 416, the system discards the blink if it does not satisfy the valid blink criterion. This ensures that only genuine blinks are considered for further analysis, enhancing the accuracy of the psychophysiological state detection. In one embodiment, the discarded data may be logged for review or used to refine the blink detection algorithm. An alternative embodiment may use the discarded data to train machine learning models to improve the accuracy of blink detection.

At operation 418, the system checks if the blink duration exceeds a duration threshold. If the duration does not exceed the threshold, the process moves to operation 422; if it does, the event is stored as a long closure at operation 420. In one embodiment, the duration threshold may be set to a value such as 3 seconds, distinguishing between a standard blink and a long closure. An alternative embodiment may use statistical analysis to determine the duration threshold based on the distribution of blink durations in the dataset.

Operation 420, the system stores the event as a long closure, which is indicative of a state such as drowsiness or prolonged cognitive load. In one embodiment, long closures are cataloged with associated metainformation, including duration and eyelid movement speeds. An alternative embodiment may involve correlating long closures with other psychophysiological data to provide a comprehensive assessment of the user's state.

At operation 422, the system stores the event as a blink. This operation catalogs standard blinks, which are indicators of psychophysiological states such as alertness or stress. In one embodiment, blinks are stored with metainformation such as blink duration, average opening speed, and maximum closing speed. An alternative embodiment may involve analyzing the distribution of blinks over time to infer patterns in the user's psychophysiological state. Following either of operation 416, operation 420, or operation 422, method 400 may end. The method 400, as described above, provides a robust framework for analyzing eyelid movements to identify blinks and long closures. By leveraging precise thresholds and incorporating metainformation, the method 400 enables the accurate detection of these events, which are enable assessing various psychophysiological states.

Referring to FIG. 5, a flowchart of a method 500 for processing a time sequence of eye gaze vectors to identify and store valid fixations is shown. The method 500 may be employed by a psychophysiological state prediction system to analyze eye movement data indicative of various psychophysiological states such as cognitive load or stress.

At operation 502, the system receives a time sequence of eye gaze vectors. These vectors represent the direction of the "virtual" vector originating from the center of the pupil and being normal to the surface of the eye. In one embodiment, the eye gaze vectors may be represented as Euler angles or coordinates in three-dimensional space. The time sequence of eye gaze vectors is captured via a user-facing camera, such as a near-infrared (NIR) camera, with a framerate corresponding to the camera's capabilities, for instance, 60 frames per second (FPS). In an alternative embodiment, the time sequence of eye gaze vectors may be received from a pre-processed dataset where the eye gaze vectors have been restored to a consistent framerate, ensuring temporal accuracy for subsequent analysis.

Proceeding to operation 504, the system removes invalid frames from the time sequence. In some embodiments, at operation 504 the system assesses the quality of the gaze data, eye opening, head and eye bounding boxes and excludes or filters out frames with a quality metric below a threshold quality. The quality of the gaze data is determined based on several parameters, including but not limited to the confidence of the eye gaze vector, the degree of eyelid openness, and the accuracy of the bounding boxes that define the regions of interest within the captured frames. In one embodiment, the quality metrics are quantified on a scale ranging from 0 to 1, where a metric of 1 signifies that the frame's data is of high quality and fully valid, while a metric of 0 indicates that the data is invalid and should be excluded from further analysis.

This binary quality assessment is employed to create a distinction between usable and unusable data. For instance, if the eye gaze vector data for a particular frame does not meet the predefined quality standards, such as being obscured or out of focus, the system assigns a quality metric of 0 to that frame. The system utilizes binary checking to determine if the data of the current frame is above the quality threshold of 0. This binary checking process involves evaluating each frame against the set quality criteria and marking it as valid or invalid accordingly. If the quality metric is 1, the frame is considered valid and is retained for further processing. Conversely, if the quality metric is 0, indicating that the frame does not meet the necessary quality standards, the frame is removed from the time sequence. In an alternative embodiment, the system may incorporate additional checks to enhance the robustness of the quality assessment. For example, the system may analyze consecutive frames to identify patterns that suggest temporary occlusions or distortions, which could affect the quality metrics temporarily. In such cases, the system may employ interpolation or other data restoration techniques to recover the valid eye gaze vectors from the affected frames, provided that the overall quality of the surrounding data supports such a recovery. Furthermore, the system may be configured to log the instances of invalid frames along with the reasons for their exclusion. This log can be used to refine the quality assessment algorithm, to train machine learning models for automated quality evaluation, or to provide feedback to the user or system operator regarding the data capture process.

At operation 506, the system converts valid eye gaze vectors to 2D eye gaze coordinates. This conversion involves calculating the points of intersection between each of the eye gaze vectors and a reference plane, known as "points-of-gaze" (POG). In one embodiment, the eye gaze coordinates for each frame are calculated using a formula that accounts for the direction components of the eye gaze vector, such as the equation given below:

$$POG(x, y) = \begin{cases} (0, 0), \text{ if } direction_2 = 0 \text{ or } quality_{gaze} = 0 \\ \left(\frac{-L}{100} * \frac{direction_0}{direction_2}, \frac{-L}{100} * \frac{direction_1}{direction_2}\right) \end{cases}$$

Where POG(x, y) are the 2D eye gaze coordinates, L is the distance from the eyes of the subject/user to the reference plane in centimeters, $direction_0$ is the component of the eye gaze vector along the x-axis, $direction_1$ is the component of the eye gaze vector along the y-axis, and $direction_2$ is the component of the eye gaze vector along the z-axis (i.e., the direction component normal to the reference plane).

At operation 508, the system selects a frame from the time sequence. This selection is part of the iterative process of analyzing each frame in the sequence to identify fixations. In one embodiment, the system processes frames sequentially, starting from the first frame after the last stored fixation or from the beginning of the sequence if no fixations have been stored yet. In another embodiment, the system may prioritize frames based on certain criteria, such as the presence of rapid eye movements or blinks, to optimize the fixation detection process.

At operation 510, the system determines the number of lost frames between the current frame and the previous frame. Lost frames are those where the data is missing or deemed invalid which may occur at operation 504. In one embodiment, the system calculates the difference between two adjacent frame numbers to determine the number of lost frames. An alternative embodiment may involve interpolating missing data based on the valid frames before and after the lost frames to maintain the continuity of the time sequence.

Operation 512 assesses whether the number of lost frames exceeds the fixation recovery threshold. If the number of lost frames is greater than the threshold, the method proceeds to operation 514, otherwise, it continues to operation 516. In one embodiment, the fixation recovery threshold may be set to a value such as 47 frames, which corresponds to the maximum number of frames that can be lost within a fixation. An alternative embodiment may adjust the threshold dynamically based on the overall quality of the data or the user's specific eye movement patterns.

At operation 514, the system discards the current fixation. This removes potentially spurious fixations. In one embodiment, the discarded fixation data may be logged for review or used to refine the fixation detection algorithm. An alternative embodiment may use the discarded data to train machine learning models to improve the accuracy of fixation detection.

At operation 516, the system determines the distance difference between the eye gaze coordinates of the current frame and the eye gaze coordinates of the previous frame. In some embodiments, operation 516 includes calculating the norm of the vectorial difference of the eye gaze coordinates to assess the stability of the gaze. In one embodiment, a fixation is defined as a sequence of frames where the intersample distance is less than 1° of visual angle. An alternative embodiment may use a dynamic threshold for the distance difference, which adjusts based on the user's typical eye movement behavior or the specific task being performed.

At operation 518, the system checks if the fixation end condition is met. If the condition is not met, the method proceeds to operation 520; if it is met, the method proceeds to operation 522. The fixation end condition may include criteria such as a significant change in eye gaze direction or the occurrence of a saccade or blink. The fixation end condition may encompass various criteria, including but not limited to a significant change in eye gaze direction, the initiation of a saccade, or the detection of a blink. In one embodiment, the system determines the end of a fixation when the distance difference between consecutive gaze coordinates exceeds a pre-determined threshold, which is indicative of the eye transitioning away from the fixation point. This threshold is established based on empirical data and is reflective of the natural variability in human gaze behavior. An alternative embodiment may incorporate additional factors into the fixation end condition, such as the duration of the fixation, which is the time elapsed since the fixation commenced. The system may be configured to recognize that fixations of an unusually long duration may be indicative of atypical behavior, such as drowsiness or distraction, and thus signal the end of a fixation.

At operation 520, the system adds the current frame to the current fixation. This operation is part of the process of building a valid fixation from the sequence of frames. In one embodiment, the system aggregates frames into a fixation until the end condition is met. An alternative embodiment may involve using a buffer to temporarily store frames that are potential candidates for inclusion in the fixation, which are then confirmed or discarded based on subsequent frames.

At operation 522, the system checks if the frames in the current fixation exceed the fixation threshold. If the number of frames does not exceed the threshold, the method proceeds to operation 514 where the current fixation is discarded. However, if the frames in the current fixation exceed the fixation threshold, the method 500 proceeds to operation 524 where the current fixation is stored in non-transitory memory. In one embodiment, the fixation threshold may be set to a value such as 6 frames, which corresponds to the minimum number of frames required for a valid fixation. An alternative embodiment may adjust the fixation threshold based on the context of the task or the user's known visual behavior.

At operation 524, the system stores the current fixation. This involves cataloging the fixation with associated metainformation, such as the start and end frames, duration, and average gaze movement speed. In one embodiment, fixations are stored in a non-transitory computer-readable medium, such as a database or a CSV file. An alternative embodiment may involve transmitting the stored fixation data to a central processing unit for real-time analysis or integration into a larger psychophysiological state prediction system.

The method 500, as described, provides a robust framework for processing eye gaze vectors to identify and store valid fixations. By leveraging precise thresholds and incorporating metainformation, the method 500 enables the accurate detection of fixations, which are may be used for downstream prediction of psychophysiological states.

Referring to FIG. 6, a flowchart of a method 600 for processing a time sequence of eye gaze vectors to identify and store valid saccades is shown. The method 600 enables the systematic analysis of eye movement data to detect rapid movements known as saccades, which are indicative of shifts in visual attention and can be used to infer psychophysiological states such as cognitive load or stress.

At operation 602, the system receives a time sequence of eye gaze vectors. These vectors represent the direction of the "virtual" vector originating from the center of the pupil captured over time using a user-facing camera, such as a near-infrared (NIR) camera. In one embodiment, the eye gaze vectors may be represented as Euler angles or coordinates in three-dimensional space. In another embodiment, the time sequence may be associated with a sampling rate corresponding to the framerate of the camera. The received data may be stored in a format such as CSV files, which include timestamped measurements of eye gaze vectors.

Proceeding to operation 604, the system removes invalid frames from the time sequence. In some embodiments, at operation 604 the system assesses the quality of the gaze data, eye opening, head and eye bounding boxes and excludes or filters out frames with a quality metric below a threshold quality. The quality of the gaze data is determined based on several parameters, including but not limited to the confidence of the eye gaze vector, the confidence of the degree of eyelid openness, and the accuracy of the bounding boxes that define the regions of interest within the captured frames. In one embodiment, the quality metrics are quantified on a scale ranging from 0 to 1, where a metric of 1 signifies that the frame's data is of high quality and fully valid, while a metric of 0 indicates that the data is invalid and should be excluded from further analysis.

This binary quality assessment is employed to create a distinction between usable and unusable data. For instance, if the eye gaze vector data for a particular frame does not meet the predefined quality standards, such as being obscured or out of focus, the system assigns a quality metric of 0 to that frame. The system utilizes binary checking to determine if the data of the current frame is above the quality threshold of 0. This binary checking process involves evaluating each frame against the set quality criteria and marking it as valid or invalid accordingly. If the quality metric is 1, the frame is considered valid and is retained for further processing. Conversely, if the quality metric is 0, indicating that the frame does not meet the necessary quality standards, the frame is removed from the time sequence. In an alternative embodiment, the system may incorporate additional checks to enhance the robustness of the quality assessment. For example, the system may analyze consecutive frames to identify patterns that suggest temporary occlusions or distortions, which could affect the quality metrics temporarily. In such cases, the system may employ interpolation or other data restoration techniques to recover the valid eye gaze vectors from the affected frames, provided that the overall quality of the surrounding data supports such a recovery. Furthermore, the system may be configured to log the instances of invalid frames along with the reasons for their exclusion. This log can be used to refine the quality assessment algorithm, to train machine learning models for automated quality evaluation, or to provide feedback to the user or system operator regarding the data capture process.

At operation 606, the system converts valid eye gaze vectors to 2D eye gaze coordinates. This conversion is performed by determining points of intersection between each of the eye gaze vectors and a reference plane. In one embodiment, the conversion may involve applying a formula that calculates the eye gaze coordinates for each frame using the direction components of the eye gaze vectors. In another embodiment, the system may utilize a eyetracker module or similar toolkit to derive the 2D eye gaze coordinates from raw NIR video frames.

At operation 608, the system selects a frame from the time sequence. The system iteratively processes each frame in the time sequence to detect changes in eye gaze direction that may signify a saccade. In one embodiment, the system may begin with the first frame following a previously identified fixation or blink. In another embodiment, the system may start with the first valid frame in the time sequence and proceed sequentially.

At operation 610, the system determines the number of lost frames between the current frame and the previous frame. Lost frames are indicative of interruptions in the data sequence (e.g., due to removal of frames by filtering operation 604), which may affect the identification of saccades. In one embodiment, the system calculates the difference between two adjacent frame numbers to determine the number of lost frames. In another embodiment, the system may incorporate error checking for timestamps to ensure that there are no large time gaps in the data.

At operation 612, the system evaluates if the number of lost frames exceeds the fixation threshold. If the number of lost frames is greater than the fixation threshold, the method proceeds to operation 614, where the current saccade is discarded. This operation is executed when the conditions for a valid saccade are not met, such as when the number of lost frames suggests that the eye movement is more likely to be a fixation. In one embodiment, the discarded saccade data may be logged for review or used to refine the saccade detection algorithm. In another embodiment, the system may use the discarded data to train machine learning models to improve the accuracy of saccade detection. Following operation 614, method 600 may end.

However, if at operation 612 the number of lost frames is determined to be below the fixation threshold method 600 continues to operation 616. In one embodiment, the fixation threshold may be set to a value such as 6 frames, based on the assumption that a fixation is a sequence of at least 6 oculometer samples with an intersample distance of less than 1° of visual angle. By ensuring no gaps in the currently detected saccade exist which are longer than a minimum duration for a fixation to occur, a probability of the currently detected saccade extending through the intervening missing frames is increased, thus reducing the probability detecting spuriously long saccades.

At operation 616, the system determines the distance difference between eye gaze coordinates of the current frame and the eye gaze coordinates of the previous frame. This operation assesses the magnitude of eye movement, which is a factor in identifying saccades. In one embodiment, the system calculates the norm of the vectorial difference of the eye gaze coordinates to determine the distance difference. In another embodiment, the system may apply a threshold for the distance difference, such as 8.73 mm at 1 meter distance, to identify significant eye movements that exceed the threshold and may indicate a saccade.

At operation 618, the system evaluates whether the saccade end condition is met. The saccade end condition may include criteria such as the total saccade angle exceeding a maximum value or the duration of the saccade reaching a pre-determined limit. In one embodiment, the saccade end condition may be based on a change in distance between two subsequent samples that is less than the threshold for a saccade. In another embodiment, the system may consider the velocity of the eye movement, with a cut-off velocity less or equal to 700°/s.

If at operation 618, the system determines the saccade end condition is not met, the method 600 proceeds to operation 620. Operation 620 adds the current frame to the current saccade and returns to operation 608. This operation is part of the iterative process of building a saccade from the sequence of eye gaze coordinates. The system continues to accumulate frames into the current saccade until the saccade end condition is met. In one embodiment, the system may count the number of frames that satisfy the saccade condition and calculate the total saccade angle as the sum of the distance differences for each frame. However, if at operation 618 the system determines that the saccade end condition is met, the method 600 continues to operation 622.

At operation 622, the system determines if the frames in the current saccade exceed the saccade threshold. The saccade threshold is a pre-determined value that defines the minimum duration for a saccade. In one embodiment, the saccade threshold may be set to a value such as 3 frames, based on the assumption that a saccade is characterized by fast eye movements lasting at least 3 samples. If the number of frames does not equal or exceed the saccade threshold, the method proceeds to operation 614, where the current saccade is discarded, and following operation 614 method 600 may end. However, if at operation 622 the system determines that the number of frames of the current saccade is equal to or greater than the saccade threshold, method 600 continues to operation 624.

At operation 624, the system stores the current saccade. This operation catalogs valid saccades, which are rapid eye movements indicative of shifts in visual attention. In one embodiment, saccades are stored with metainformation such as saccade duration, average saccade velocity, and maximum saccade angle. In another embodiment, the system may analyze the distribution of saccades over time to infer patterns in the user's psychophysiological state. Following operation 624, method 600 may end. The method 600 enables the accurate detection of saccades, by leveraging precise and data quality assessments.

Referring to FIG. 7, a method 700 for analyzing eye gaze data to calculate stationary gaze entropy and gaze transition entropy is shown. The method 700 provides a systematic approach for quantifying visual scanning behavior during tasks with high visuospatial demand, such as driving or simulated aviation. By leveraging eye gaze data, the method 700 enables the assessment of cognitive load and psychophysiological states of individuals based on their visual scanning patterns.

At operation 702, the system accesses labeled fixation events within a pre-determined time window. This operation involves retrieving fixation data that has been previously identified and labeled from a sequence of eye gaze vectors. In some embodiments, the labeled fixation events are characterized by a sequence of at least six oculometer samples with an intersample distance of less than 1° of visual angle, as described in more detail herein. In an alternative embodiment, the fixation events may be accessed from a database where they have been stored after being processed by one or more operations disclosed herein.

Proceeding to operation 704, the system obtains 2D eye gaze coordinates for each fixation event on a projection plane. This operation involves calculating the points of intersection between the eye gaze vectors and a reference plane, which may be a screen or any other surface of interest. In one embodiment, the 2D eye gaze coordinates are determined from the eye gaze vector, which comprises a vector encoding the x, y, and z coordinates of direction of gaze of the user.

At operation 706, the system converts the 2D eye gaze coordinates to pixels. This conversion enables discretizing the eye gaze coordinates of the fixation event and preparing them for entropy calculation. In one embodiment, the conversion is performed using a predefined scale factor, such as 37.7952755906, to transform the coordinates from centimeters to pixels. In another embodiment, the conversion may be adjusted based on the resolution and dimensions of the projection plane to ensure accurate representation of the fixation points in pixel space.

At operation 708, the system determines bounds for each fixation event. This operation defines the spatial extent of each fixation within the projection plane. In one embodiment, the fixation bounds are determined by identifying the maximum and minimum x and y coordinates of the fixation points, thereby establishing an area of interest for each fixation. An alternative embodiment may involve calculating the area's vertical and horizontal diameters to further characterize the fixation bounds.

At operation 710, the system partitions the region of the projection plane bounded by the fixation bounds into a plurality of pixel bins of pre-determined size. This operation creates a grid-like structure over the area of interest, with each bin representing a discrete state space for the fixation points. In one embodiment, the pixel bins may be set to a size of 30×30 pixels, to ensure a balance between resolution and computational efficiency. In another embodiment, the size of the pixel bins may be adjusted based on the density of fixation points and the desired granularity of the entropy measures.

At operation 712, the system determines for each of the plurality of pixel bins a corresponding number of 2D eye gaze coordinates located therein. This operation quantifies the distribution of fixation points across the pixel bins. In one embodiment, the system counts the number of fixation points that fall within each bin, effectively organizing the fixation coordinates into spatial bins. An alternative embodiment may involve using a search algorithm to associate each fixation point with the corresponding bin based on its pixel coordinates.

At operation 714, the system calculates the stationary gaze entropy (Hs) and the gaze transition entropy (Hc) from the numbers of 2D eye gaze coordinates in each of the plurality of pixel bins. This operation applies Shannon's entropy equation to the probability distribution of fixation coordinates to calculate Hs, which represents the average level of uncertainty in the spatial distribution of a sequence of fixations. In one embodiment, Hs is calculated based on the proportion of fixations landing on a given state space within the pre-determined time window. He may be calculates by applying the conditional entropy equation to Markov chain matrices of fixation transitions, providing an average measure of predictability of visual scanning patterns. Higher entropy suggests less structured or a more random pattern of scanning behavior, which can be indicative of cognitive load or fatigue. In one example, the stationary gaze entropy (Hs) may be determined according to the below equation:

$$H_s(x) = -\sum_{i=1}^{N} p(i) \cdot \log_2 p(i),$$

Where Hs is the stationary gaze entropy of a set of fixations x within the pre-determined time window. N is the total number of fixations within the pre-determined time window x, and p is the proportion of fixations landing on a given state space (i.e. pixel bin) within x.

In another example, the gaze transition entropy He may be determined according to the below equation:

$$H_c(x) = -\sum_{i=1}^{N} p(i) \left[ \sum_{j=1}^{N} p(i \mid j) \cdot \log_2 p(i \mid j) \right],\ i \neq j,$$

where p(i) is the stationary distribution of fixation locations, p(i|j) is the probability of transitioning to pixel bin j given current position of pixel bin i, and i≠j denotes exclusion of transitions within the same pixel bin from the inner summation.

Following operation 714, method 700 may end. The method 700, as described, enables determination of quantitative measures of visual scanning behavior. By calculating stationary and transition gaze entropy, the method 700 offers a technical solution for characterizing and quantifying visual scanning patterns in naturalistic environments, thereby enhancing the understanding and interpretation of a user's psychophysiological state.

The disclosure also provides support for a method comprising: capturing, via a user-facing camera, a sequence of eye gaze vectors and eyelid openness levels over time, determining a plurality of second order eye movement metrics from the eye gaze vectors and eyelid openness levels, wherein the plurality of second order eye movement metrics are indicative of discrete eye behaviors, transforming the plurality of second order eye movement metrics into a machine readable representation of the plurality of second order eye movement metrics within a pre-determined time window, and predicting, via a mathematical model, one or more psychophysiological states using the machine readable representation of the plurality of second order eye movement metrics. In a first example of the method, determining the plurality of second order eye movement metrics comprises, converting the eye gaze vectors to a sequence of eye gaze coordinates by determining points of intersection between each of the eye gaze vectors and a reference plane. In a second example of the method, optionally including the first example, transforming the plurality of second order eye movement metrics into the machine readable representation includes calculating a number of blinks, a number of fixations, and an overall fixation time within the pre-determined time window. In a third example of the method, optionally including one or both of the first and second examples the method further comprising: calculating a fixation entropy for fixations identified in the sequence of eye gaze vectors, the fixation entropy comprising stationary gaze entropy (Hs) and gaze transition entropy (Hc), wherein Hs is calculated based on a probability distribution of fixation coordinates within the pre-determined time window, and He is calculated based on Markov chain matrices of fixation transitions in the pre-determined time window. In a fourth example of the method, optionally including one or more or each of the first through third examples, determining the plurality of second order eye movement metrics further includes identifying blinks based on the eyelid openness levels, wherein a blink comprises a contiguous portion of frames from the sequence of eyelid openness levels satisfying a blink criterion based on calculated differences between adjacent eyelid openness levels for each frame of the contiguous portion of frames. In a fifth example of the method, optionally including one or more or each of the first through fourth examples, the method further comprises: assessing quality of the sequence of eye gaze vectors and eyelid openness by calculating quality metrics for each frame of the sequence, wherein the quality metrics are based on a binary evaluation of a validity of head and eye bounding boxes, eyelid quality, and eye gaze quality, and wherein a quality metric value of 1 indicates valid data and a value of 0 indicates invalid data, and discarding frames with invalid data from the sequence prior to determining the plurality of second order eye movement metrics.

The disclosure also provides support for a method comprising: receiving a time sequence of eye gaze vectors and eyelid openness levels of a user, transforming the time sequence of eye gaze vectors and eyelid openness levels to a sequence of discrete eye behaviors, including one or more of saccades, fixations, blinks, and long closures, determining metainformation associated with each of the discrete eye behaviors, converting the sequence of discrete eye behaviors into a machine readable representation of eye behaviors using a sliding time window, and mapping the machine readable representation of eye behaviors via a machine learning model to one or more psychophysiological states. In a first example of the method, transforming the sequence of eye gaze vectors and eyelid openness levels to the sequence of discrete eye behaviors comprises, converting the eye gaze vectors to a sequence of eye gaze coordinates by determining points of intersection between each of the eye gaze vectors and a reference plane. In a second example of the method, optionally including the first example, transforming the sequence of eye gaze vectors into a saccade or fixation comprises: labeling a first contiguous portion of the sequence of eye gaze coordinates as a saccade responsive to a change in eye gaze direction within the first contiguous portion of the sequence of eye gaze coordinates exceeding a pre-determined angular velocity threshold, and labeling a second contiguous portion of the sequence of eye gaze coordinates as a fixation responsive to eye gaze coordinates of the second contiguous portion of the sequence of eye gaze coordinates remaining within a pre-determined range for a duration exceeding a predetermined fixation duration threshold. In a third example of the method, optionally including one or both of the first and second examples, transforming the sequence of eye gaze vectors and eyelid openness levels to the sequence of discrete eye behaviors further comprises: identifying a blink as a first contiguous portion of the sequence of eyelid openness in which the eyelid openness is below a pre-determined threshold for less than a threshold duration of time, and identifying a long closure as a second contiguous portion of the sequence of eyelid openness in which the eyelid openness is below the pre-determined threshold for greater than the threshold duration of time. In a fourth example of the method, optionally including one or more or each of the first through third examples the method further comprising: calculating for each identified blink and long closure metainformation including at least blink duration, eyelid close speed, and eyelid open speed, and determining a start and an end of each blink and long closure based on a velocity threshold of eyelid movement, wherein a velocity at the start and end of a blink is greater than a pre-determined velocity threshold, and a velocity at a start and an end of a long closure is less than the pre-determined velocity threshold. In a fifth example of the method, optionally including one or more or each of the first through fourth examples, the eye gaze vectors encode a direction in three-dimensional space of a virtual vector originating from a center of a pupil of the user and being normal to a surface of an eye of the user. In a sixth example of the method, optionally including one or more or each of the first through fifth examples, the metainformation includes at least one of a length of each of the discrete eye behaviors, an average gaze movement speed, and gaze fluctuation boundaries. In a seventh example of the method, optionally including one or more or each of the first through sixth examples, the machine readable representation includes one or more of a number of blinks, a number of fixations, an overall fixation time, and an average fixation time for the sliding time window.

The disclosure also provides support for a system for detecting psychophysiological states from eye movement data, the system comprising: a camera configured to capture a sequence of eye gaze vectors and eyelid openness levels over time, a non-transitory memory storing instructions, and a machine learning model, and a processor communicably coupled to the camera and the non-transitory memory, the processor, when executing the instructions, configured to: determine a plurality of second order eye movement metrics from the eye gaze vectors and eyelid openness levels, wherein the plurality of second order eye movement metrics are indicative of discrete eye behaviors, transform the plurality of second order eye movement metrics into a machine readable representation of the plurality of second order eye movement metrics within a pre-determined time window, and predict one or more psychophysiological states using the machine learning model based on the machine readable representation of the plurality of second order eye movement metrics. In a first example of the system, the processor is further configured to convert the eye gaze vectors to a sequence of eye gaze coordinates by determining points of intersection between each of the eye gaze vectors and a reference plane. In a second example of the system, optionally including the first example, the processor is further configured to label a contiguous portion of the sequence of eye gaze coordinates as a saccade or fixation based on changes in eye gaze direction and duration within pre-determined thresholds. In a third example of the system, optionally including one or both of the first and second examples, the processor is further configured to calculate fixation entropy for fixations identified in the sequence of eye gaze vectors, the fixation entropy comprising stationary gaze entropy (Hs) and gaze transition entropy (Hc), wherein Hs is calculated based on a probability distribution of fixation coordinates within a pre-determined duration, and He is calculated based on Markov chain matrices of fixation transitions in the pre-determined duration. In a fourth example of the system, optionally including one or more or each of the first through third examples, the processor is further configured to assess quality of the sequence of eye gaze vectors and eyelid openness by calculating quality metrics for each frame of the sequence, wherein the quality metrics are based on a binary evaluation of a validity of head and eye bounding boxes, eyelid quality, and eye gaze quality, and wherein a quality metric value of 1 indicates valid data and a value of 0 indicates invalid data. In a fifth example of the system, optionally including one or more or each of the first through fourth examples, the processor is further configured to identify blinks and long closures in the sequence of eyelid openness levels by applying pre-determined thresholds for eyelid openness and duration, and to calculate metainformation associated with each identified blink and long closure, including at least blink duration, eyelid close speed, and eyelid open speed.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors.

While the foregoing is directed to embodiments of the present disclosure, other and further embodiments of the disclosure may be devised without departing from the basic scope thereof, and the scope thereof is determined by the claims that follow.

The invention claimed is:

1. A method comprising:

capturing, via a user-facing camera, a sequence of eye gaze vectors and eyelid openness levels over time;

determining a plurality of second order eye movement metrics from the eye gaze vectors and eyelid openness levels, wherein the plurality of second order eye movement metrics are indicative of discrete eye behaviors;

transforming the plurality of second order eye movement metrics into a machine readable representation of the plurality of second order eye movement metrics within a pre-determined time window;

predicting, via a mathematical model, one or more psychophysiological states using the machine readable representation of the plurality of second order eye movement metrics, and calculating a fixation entropy for fixations identified in the sequence of eye gaze vectors, the fixation entropy comprising stationary gaze entropy (Hs) and gaze transition entropy (Hc), wherein Hs is calculated based on a probability distribution of fixation coordinates within the pre-determined time window, and Hc is calculated based on Markov chain matrices of fixation transitions in the pre-determined time window.

2. The method of claim 1, wherein determining the plurality of second order eye movement metrics comprises, converting the eye gaze vectors to a sequence of eye gaze coordinates by determining points of intersection between each of the eye gaze vectors and a reference plane.

3. The method of claim 1, wherein transforming the plurality of second order eye movement metrics into the machine readable representation includes calculating a number of blinks, a number of fixations, and an overall fixation time within the pre-determined time window.

4. The method of claim 1, wherein determining the plurality of second order eye movement metrics further includes identifying blinks based on the eyelid openness levels, wherein a blink comprises a contiguous portion of frames from the sequence of eyelid openness levels satisfying a blink criterion based on calculated differences between adjacent eyelid openness levels for each frame of the contiguous portion of frames.

5. The method according to claim 1, further comprising:

assessing quality of the sequence of eye gaze vectors and eyelid openness by calculating quality metrics for each frame of the sequence, wherein the quality metrics are based on a binary evaluation of a validity of head and eye bounding boxes, eyelid quality, and eye gaze quality, and wherein a quality metric value of 1 indicates valid data and a value of 0 indicates invalid data; and discarding frames with invalid data from the sequence prior to determining the plurality of second order eye movement metrics.

6. A system for detecting psychophysiological states from eye movement data, the system comprising:

a camera configured to capture a sequence of eye gaze vectors and eyelid openness levels over time;

a non-transitory memory storing instructions, and a machine learning model; and a processor communicably coupled to the camera and the non-transitory memory, the processor, when executing the instructions, configured to:

determine a plurality of second order eye movement metrics from the eye gaze vectors and eyelid openness levels, wherein the plurality of second order eye movement metrics are indicative of discrete eye behaviors;

transform the plurality of second order eye movement metrics into a machine readable representation of the plurality of second order eye movement metrics within a pre-determined time window; and predict one or more psychophysiological states using the machine learning model based on the machine readable representation of the plurality of second order eye movement metrics, psychophysiological states including one or more of cognitive load, stress, and fatigue, wherein the processor is further configured to assess quality of the sequence of eye gaze vectors and eyelid openness by calculating quality metrics for each frame of the sequence, wherein the quality metrics are based on a binary evaluation of a validity of head and eye bounding boxes, eyelid quality, and eye gaze quality, and wherein a quality metric value of one of 0 and 1 indicates valid data and a value of the other of 0 and 1 indicates invalid data.

7. The system of claim 6, wherein the processor is further configured to convert the eye gaze vectors to a sequence of eye gaze coordinates by determining points of intersection between each of the eye gaze vectors and a reference plane.

8. The system of claim 6, wherein the processor is further configured to label a contiguous portion of the sequence of eye gaze coordinates as a saccade or fixation based on changes in eye gaze direction and duration within predetermined thresholds.

9. The system of claim 6, wherein the processor is further configured to calculate fixation entropy for fixations identified in the sequence of eye gaze vectors, the fixation entropy comprising stationary gaze entropy (Hs) and gaze transition entropy (Hc), wherein Hs is calculated based on a probability distribution of fixation coordinates within a pre-determined duration, and Hc is calculated based on Markov chain matrices of fixation transitions in the pre-determined duration.

10. The system of claim 6, wherein the processor is further configured to identify blinks and long closures in the sequence of eyelid openness levels by applying pre-determined thresholds for eyelid openness and duration, and to calculate metainformation associated with each identified blink and long closure, including at least blink duration, eyelid close speed, and eyelid open speed.

* * * * *